(12) United States Patent
Pellen et al.

(10) Patent No.: US 8,277,429 B2
(45) Date of Patent: Oct. 2, 2012

(54) ABSORBENT PRODUCT HAVING A MINIATURE MODEL

(75) Inventors: Tanguy Yann Pellen, Beijing (CN); Jing Zhang, Beijing (CN); Xiaofeng Wang, Beijing (CN)

(73) Assignee: The Proctor and Gamble Company, Cincinnati, OH (US)

( * ) Notice: Subject to any disclaimer, the term of this patent is extended or adjusted under 35 U.S.C. 154(b) by 447 days.

(21) Appl. No.: 12/469,929

(22) Filed: May 21, 2009

(65) Prior Publication Data

US 2009/0312733 A1    Dec. 17, 2009

Related U.S. Application Data

(60) Provisional application No. 61/132,218, filed on Jun. 17, 2008.

(51) Int. Cl.
*A61F 13/15* (2006.01)
*A61L 15/00* (2006.01)

(52) U.S. Cl. .............. 604/385.02; 604/385.01; 206/438; 206/440

(58) Field of Classification Search ............. 604/385.02, 604/385.01; 206/438, 440
See application file for complete search history.

(56) References Cited

U.S. PATENT DOCUMENTS

| | | | |
|---|---|---|---|
| 6,454,095 | B1 | 9/2002 | Brisebois et al. |
| 2006/0129115 | A1 | 6/2006 | Visscher et al. |
| 2007/0295629 | A1 | 12/2007 | Adriaanse et al. |
| 2008/0011632 | A1 | 1/2008 | Albino |
| 2008/0099360 | A1 | 5/2008 | Smith et al. |
| 2008/0110782 | A1 | 5/2008 | Burgdorf et al. |

FOREIGN PATENT DOCUMENTS

EP    0 986 996 A2    3/2000

OTHER PUBLICATIONS

PCT International Search Report, mailed Oct. 2, 2009, 7 pages.

*Primary Examiner* — Jacqueline F. Stephens
(74) *Attorney, Agent, or Firm* — Andres E. Velarde; David M. Weirich; Brian M. Bolam

(57) ABSTRACT

Absorbent product including a package, at least one absorbent article and a miniature model.

21 Claims, 6 Drawing Sheets

ABSORBENT PRODUCT HAVING A MINIATURE MODEL

CROSS REFERENCE TO RELATED APPLICATION

This application claims the benefit of U.S. Provisional Application No. 61/132,218, filed Jun. 17, 2008.

FIELD OF THE INVENTION

The present invention relates to an absorbent product including a package, and more particularly to an absorbent product including a package, at least one absorbent article contained therein, and a miniature model.

BACKGROUND OF THE INVENTION

Consumer products are often marketed to consumers at the point of sale in packages, such as boxes, containers, flexible bags, blister packs, cartons, and the like. The packages can be attractive and eye-catching so that consumers may stop and consider purchasing the packaged products. Manufacturers also desire to make a product package informative so that consumers can obtain accurate information about a product from looking at and/or handling the package.

In the field of absorbent articles such as sanitary napkins and diapers, it can be difficult to deliver accurate product information regarding the absorbent article by the package alone. Some packages can have an image of the absorbent article on the exterior surface, but such an image may not be sufficient to fully deliver features such as undulations and channels to consumers.

As such, there is a need for packaging for absorbent articles that is eye-catching to consumers at the point of sale. Additionally, there remains a need for packaging that not only provides an outstanding appearance that causes consumers to stop and look, but also has structural features that help consumers understand the feature of the product inside the package. Especially, there remains a need in the field of absorbent articles such as sanitary napkins or pantiliners.

SUMMARY OF THE INVENTION

The present invention relates to an absorbent product comprising (i) a package, (ii) at least one absorbent article and (iii) a miniature model. The package has an exterior surface and an interior surface. The interior surface defines an interior space. The absorbent article is contained within the interior space. The absorbent article has a body-facing surface and a garment-facing surface. The absorbent article comprises at least one dimensional feature and a periphery viewable from the body-facing surface. The miniature model has a first surface and a second surface opposing the first surface. The first surface has a mimic portion adapting to depict at least a part of the dimensional feature of the absorbent article.

DETAILED DESCRIPTION OF THE INVENTION

Figure 1:
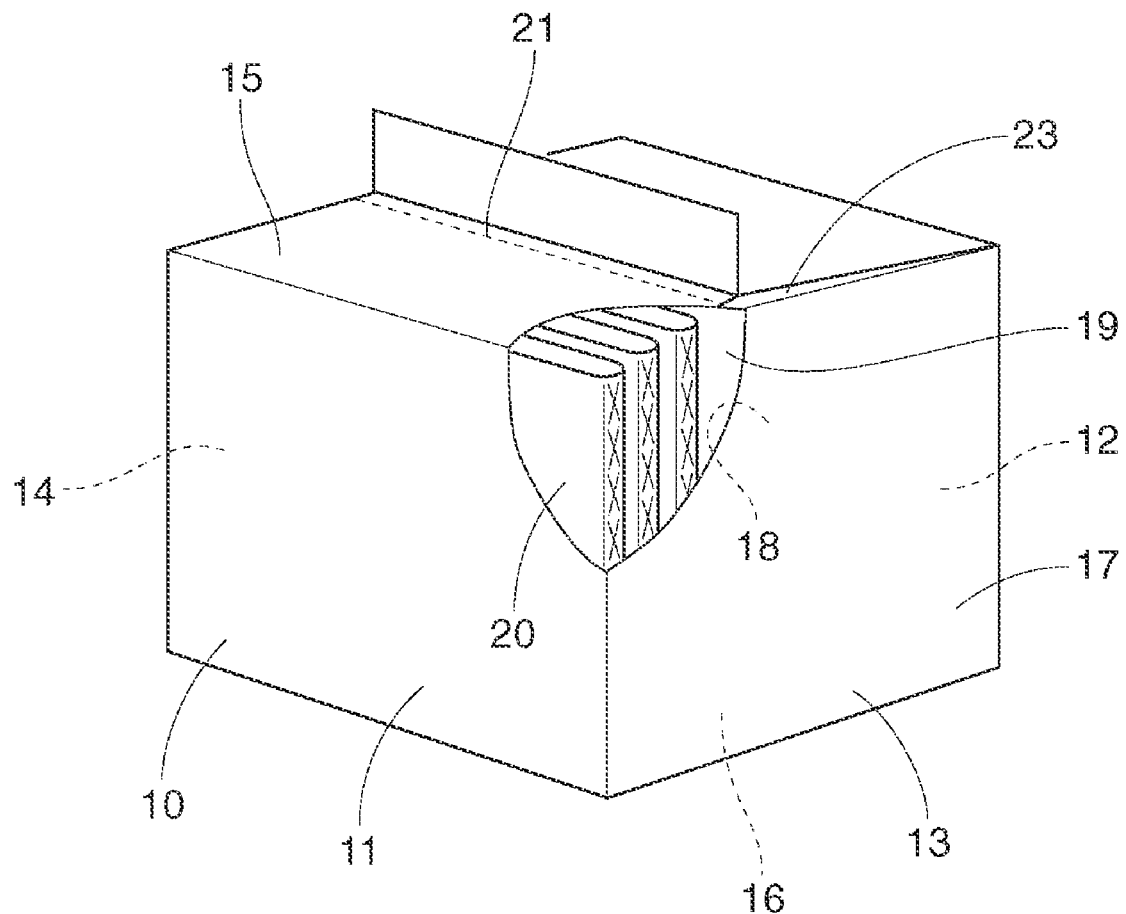
FIG. 1 is a perspective view of a package.

The present invention relates to an absorbent product having a package, an absorbent article disposed therein, and a miniature model. In certain embodiments, the absorbent product can help consumers understand the product features and the benefits of the absorbent article contained in the package without actually touching the absorbent article in the retail outlet. Additionally or alternatively, the absorbent product can display the absorbent article impressively to draw consumers' attention. The absorbent product can also attract consumers in the retail outlet to encourage them to purchase the absorbent product.

Herein, "comprise" and "include" mean that other elements and/or other steps which do not affect the end result can be added. Each of these terms encompasses the terms "consisting of" and "consisting essentially of".

Herein, "absorbent article" refers to articles that absorb and contain body exudates or discharges such as body fluids, and is intended to include sanitary napkins, pantiliners, tampons, interlabial devices, pessaries, contraceptives, diapers (both for baby and adult incontinence), training pants and adult incontinence pads (and other articles worn in the crotch region of a garment), sweat-absorbent underarm pads, nursing pads, human waste management devices and the like.

Herein, "disposable" refers to articles that are intended to be discarded after a single use, composted, or otherwise disposed of in an environmentally compatible manner. That is, they are not intended to be laundered or otherwise restored or reused as an absorbent article.

Herein, "sanitary napkin" refers to articles which are worn by females adjacent to the pudendal region that are intended to absorb and contain the various exudates that are discharged from the body (e.g., blood, menses, and urine).

Herein, "body-facing surface" refers to a surface of an absorbent article and/or its component members that faces the body of the wearer when the absorbent article is worn. "External surface" refers to the surface opposite the body-facing surface of the absorbent articles and/or component members that face away from the wearer when the absorbent article is worn.

The invention is described below in relation to one embodiment of the present invention that is an absorbent product comprising a package for containing disposable absorbent articles. Disposable absorbent articles can be individually wrapped and sealed in pouches, packets, or other outer wrapping and packaged for retail sale in the package. For example, sanitary napkins can be folded, wrapped in an outer film wrapper, and stacked in package for sale to consumers at a retail outlet. While the invention is described with respect to disposable absorbent products, the invention can be applied to other consumer products as desired.

The present invention relates to an absorbent product comprising a package, at least one disposable absorbent article contained therein, and a miniature model. In certain embodiments, the miniature model can be attached to the package.

FIG. 1 illustrates a perspective view of a package containing a plurality of sanitary napkins. A part of the package is cut off to show the absorbent articles inside the package. FIG. 1 shows a package 10 in the shape of a parallelepiped, having a front panel 11, a rear panel 12 opposing to the front panel 11, a pair of side panels 13 and 14, a top panel 15 and a bottom panel 16. The package 10 has an exterior surface 17 and an interior surface 18. The interior surface 18 forms an enclosure having an interior space 19. The package 10 contains a plurality of wrapped sanitary napkins 20 which forms a stack.

Herein, "package" refers to a means for containing one or more absorbent articles. The package can take any suitable size, shape and structure known in the art. In certain embodiments, the package can be a flexible bag having a parallelepiped shape that contains at least one absorbent article. Additionally or alternatively, the package can have a cubic shape or a columnar shape.

The package 10 may be formed by any suitable material and can take any structure known in the art. Materials used to construct packages may include, but are not limited to, polymeric films, such as polypropylene films, polyethylene films, co-extruded polyethylene and ethylene vinyl acetate films and the like, paperboards and coated paper. The package material may be of biodegradable, recyclable, non-biodegradable or non-recyclable materials. In certain embodiments, the package 10 can be constructed as cartons and/or flexible packages, such as pouches and bags. As shown in FIG. 1, the package 10 can be a flexible bag, such as, e.g., a bag formed by a thin polyethylene film material. In certain embodiments, the package 10 may be formed through manipulation of a single sheet of material, such as folding, by attaching multiple sheets to one another or a combination thereof. Additionally or alternatively, the package 10 may be sealed or adhered in any suitable manner, such as by heat seal, ultrasonics, adhesives, hook and loop fasteners and the like.

In certain embodiments, an opening device for retrieving an absorbent article 20 may be provided at a suitable location on the package 10. As shown in FIG. 1, an opening device 21 for retrieving a sanitary napkin 20 is provided on the top panel 15 of the package 10. The opening device 21 may be provided such that the sanitary napkins 20 can be retrieved easily by consumers. The opening device 21 can be any suitable structure, shape and dimension. For example, in certain embodiments, the opening device 21 may include a line of weakness that extends within the top panel 15. The line of weakness may include a line of perforation formed in the top panel 15. Additionally or alternatively, the top portions of the package 10 can be closed by forming a top gusset structure 23 which is formed by sealing the film.

Figure 2:
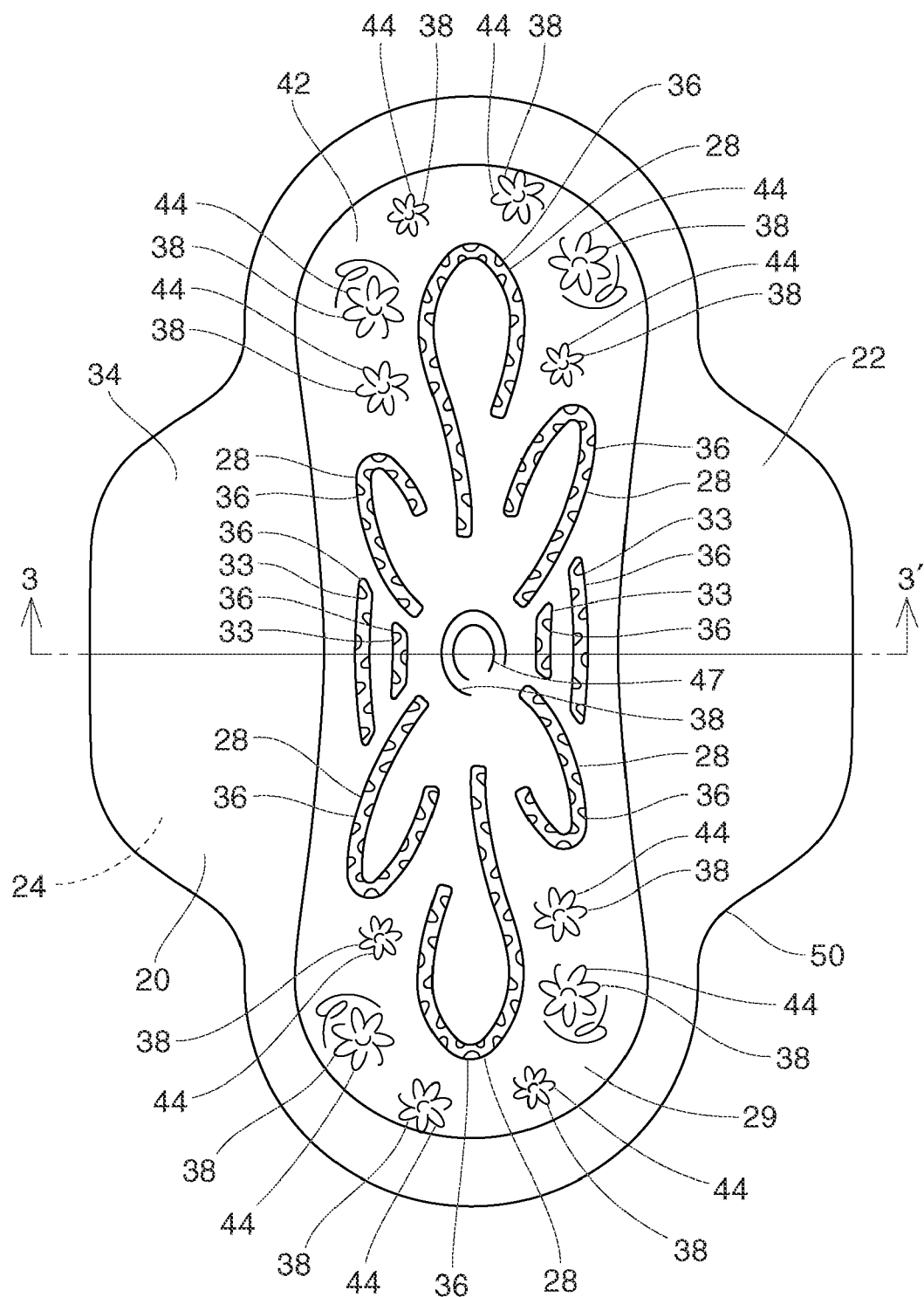
FIG. 2 is a top plan view of an absorbent article.
Figure 3:
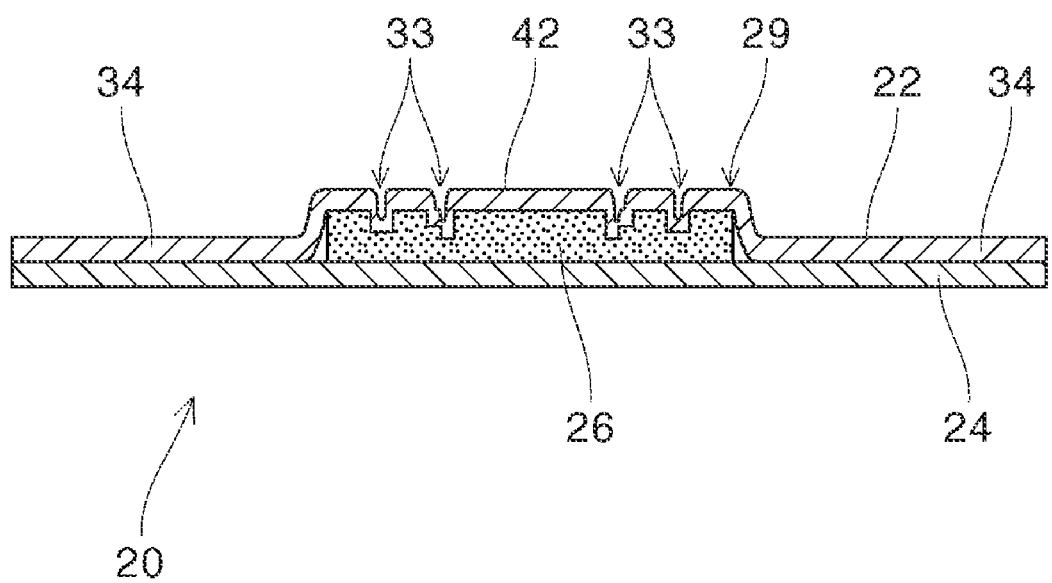
FIG. 3 is a cross-sectional view of the absorbent article of FIG. 2 along line 3-3'.

FIG. 2 illustrates a top plan view of a sanitary napkin 20. FIG. 3 illustrates a cross-sectional view of sanitary napkin 20 of FIG. 2 along line 3-3'. Sanitary napkin 20 comprises a topsheet 22, a backsheet 24 and an absorbent core 26 disposed between the topsheet 22 and the backsheet 24. Any individual layers of their component members can have a body-facing surface and an external surface opposed to the body-facing surface.

Any suitable topsheet 22 can be used. In certain embodiments, the topsheet 22 may be compliant, soft feeling, and non-irritating to the wearer's skin. Additionally or alternatively, the topsheet 22 may be liquid permeable or pervious, such as to permit discharged materials to readily penetrate through its thickness. The topsheet 22 may be manufactured from any suitable material, such as for example woven and nonwoven materials (e.g., a nonwoven web of fibers); polymeric materials such as apertured formed thermoplastic films, apertured plastic films, and hydroformed thermoplastic films; porous foams; reticulated foams; reticulated thermoplastic films; and thermoplastic scrims. When the topsheet 22 includes a nonwoven web, the web may be manufactured by any suitable technique. For example, the web may be spunbonded, carded, wet-laid, melt-blown, hydroentangled, combinations of the above, or the like. In certain embodiments, the body-facing surface of the topsheet 22 can be made hydrophilic by treatment with a surfactant. In certain embodiments, the external surface of the topsheet 22 may be attached to the absorbent core 26. Additionally or alternatively, the topsheet 22 may be attached to the backsheet 24.

Generally, the backsheet 24 may be impervious to discharged materials such that the backsheet 24 may prevent discharged materials absorbent and contained in the absorbent core 26 from leaking out of the sanitary napkin 20. Backsheet 24 can be manufactured from any suitable materials, such as a thin plastic film or other flexible liquid impervious materials. In certain embodiments, the backsheet 24 may include woven or nonwoven materials, polymeric films such as thermoplastic films of polyethylene or polypropylene, or composite materials such as a film-coated nonwoven material. The backsheet 24 may include a single layer material, or plurality of layer materials. The backsheet 24 may be a single layer polyethylene film or may be a double layer consisting of a polyethylene film and nonwoven. The backsheet 24 may have a microporous structure which permits vapors to escape from the absorbent core (called "breathable backsheet") while still preventing discharged materials from passing through the backsheet 24.

The absorbent core 26 is typically capable of receiving, absorbing and/or retaining discharged materials from the body. In certain embodiments, the absorbent core 26 may be compressible, conformable and non-irritating to the wearer's skin. The absorbent core 26 may be formed by a single layer material or a plurality of layer materials. The absorbent core 26 may include suitable liquid-absorbent materials, such as comminuted wood pulp, which is generally referred to as "airfelt." In certain embodiments, the absorbent core 26 may comprise a multi-bonded air laid nonwoven material.

The absorbent core 26 may be manufactured in a wide variety of sizes and shapes. The absorbent core 26 thus can take any shape in its top plan view. Shapes for the absorbent core 26 may include an oval, a rectangle, an hourglass, a circle, a square, and any other shape.

The absorbent article 20 has a peripheral boundary 50. The peripheral boundary 50 forms an outline of the absorbent article 20.

The absorbent article 20 can include a dimensional feature, such as a three-dimensional feature and/or a two-dimensional feature. As shown in FIG. 2, the absorbent article 20 can include a three-dimensional feature 36 on the body-facing surface 42. In certain embodiments, the three-dimensional feature 36 may be a structure having a functional property such as fluid blocking and fluid absorption. The three-dimensional feature can include, for example, an embossment, a perforation, a channel, a convex portion, a concave portion, an aperture, a peripheral boundary, and the like. In certain embodiments, the three-dimensional feature 36 may extend from the topsheet 22 to the absorbent core 26 (e.g., a channel, an embossment, a perforation, and the like). Additionally or alternatively, the three-dimensional feature 36 may be provided on the topsheet 22 (e.g., an aperture, and the like). In certain embodiments, the three-dimensional feature 36 may be formed by the thickness of the absorbent core 26 of the absorbent article 20 (e.g., a concave portion, a convex portion, a perforation, and the like). Additionally or alternatively, the three-dimensional feature 36 may be formed by the overall shape of the absorbent article (e.g., a peripheral boundary, and the like). For example, in certain embodiments, such as shown in FIGS. 2 and 3, the sanitary napkin 20 can comprise a plurality of channels 28 and 33. In addition, as shown in FIGS. 2 and 3, the sanitary napkin 20 comprises a convex portion 29 that can be formed by the thickness of the absorbent core 26.

The three-dimensional feature 36 can provide technical and/or aesthetic information to a consumer. For example, a channel or an embossment can reduce leakage from the absorbent article 20 and/or can provide the perception of reduced leakage to a consumer. Consumers may feel satisfied to see the presence of a channel and/or an embossment. In certain embodiments, when such a channel and an embossment have an aesthetic element (e.g., a plurality of channels 28 and 33 forms a blossom-like pattern as shown in FIG. 2), the absorbent article 20 can be visually well-received by consumers. Additionally or alternatively, the thickness of the absorbent core 26 can serve to absorb the fluid discharged from the body and consumers may feel relieved when viewing this thickness.

In certain embodiments, the absorbent article 20 may include a two-dimensional feature 38. The two-dimensional feature refers to an aesthetic or visual element that may attract consumers. In certain embodiments, the two-dimensional feature 38 may be a color signal. The term "color signal" may refer, but is not limited, to a colored part of the absorbent article 20 that is differentiated from the rest of the absorbent article 20. In certain embodiments, such a color signal may comprise a pattern, character information, and the like.

The color signal can be any suitable color, such as, for example, blue, green, light green, yellow green, pink, purple, black, brown, red, yellow, or variations thereof, and the like. In certain embodiments, a plurality of colors may be used as the color signal. The color signal can be provided on any suitable component of the absorbent article such as a topsheet, a backsheet, an absorbent core, an insert provided between the topsheet and the absorbent core, and the like such that the color signal is visible from the body-facing side of the absorbent article. The color can be printed by any conventional printing methods or technologies known in the art, including, but not limited to, gravure printing, flexo printing, offset printing, ink jet printing, and the like.

In certain embodiments, the color signal may be beneficial to a customer because colors can affect human mentality. For example, cold colors such as blue and green may give a clean and fresh impression to a consumer, warm colors such as orange and pink may be stimulating and inviting to a consumer, and natural colors such as green, yellow green and brown may relieve a consumer of stress and uneasiness because such colors may remind the consumers of nature.

As shown in FIG. 2, the sanitary napkin 20 can include a plurality of color signals 44 of a flower petal pattern such as, e.g., a yellow green flower petal pattern, dispersed on the topsheet 22. Additionally or alternatively, the sanitary napkin 20 can further comprise a color signal 47 of a yellow green U-shape pattern in the center of the sanitary napkin 20. As shown in FIG. 2, the patterns and the yellow green color can give a "natural" impression to consumers.

In certain embodiments, the color signal is visible from the body-facing surface of the absorbent article. When the color signal is provided on the topsheet 22 of the sanitary napkin 20, it may be perceivable from the body-facing side of the absorbent article 20 directly. When the color signal is provided on the absorbent core 26, it can be perceivable from the body-facing side of the sanitary napkin 20 through the topsheet 22. When the color signal is provided on the backsheet 24 in the peripheral region 34 outside the absorbent core 26, the color signal may be perceivable through the topsheet 22. In certain embodiments, the color signal may be printed on another material than the topsheet 22 or the backsheet 24 (e.g. a polymeric film, a sheet of paper, and the like) and the printed material may be joined on or placed between the topsheet 22, the backsheet 24 or the absorbent core 26.

In certain embodiments, when the sanitary napkins 20 are wrapped by an outer wrapper or folded inside, the three-dimensional feature 36 and/or the two-dimensional feature 38 on the body-facing surface may not be perceivable from outside. As shown in FIG. 1, when the sanitary napkins 20 are contained in the package 10, the three-dimensional feature 36 and the two-dimensional feature 38 are less perceivable from outside. Therefore, the manufacturer may find it difficult to accurately convey information about the absorbent article to consumers.

Figure 4:
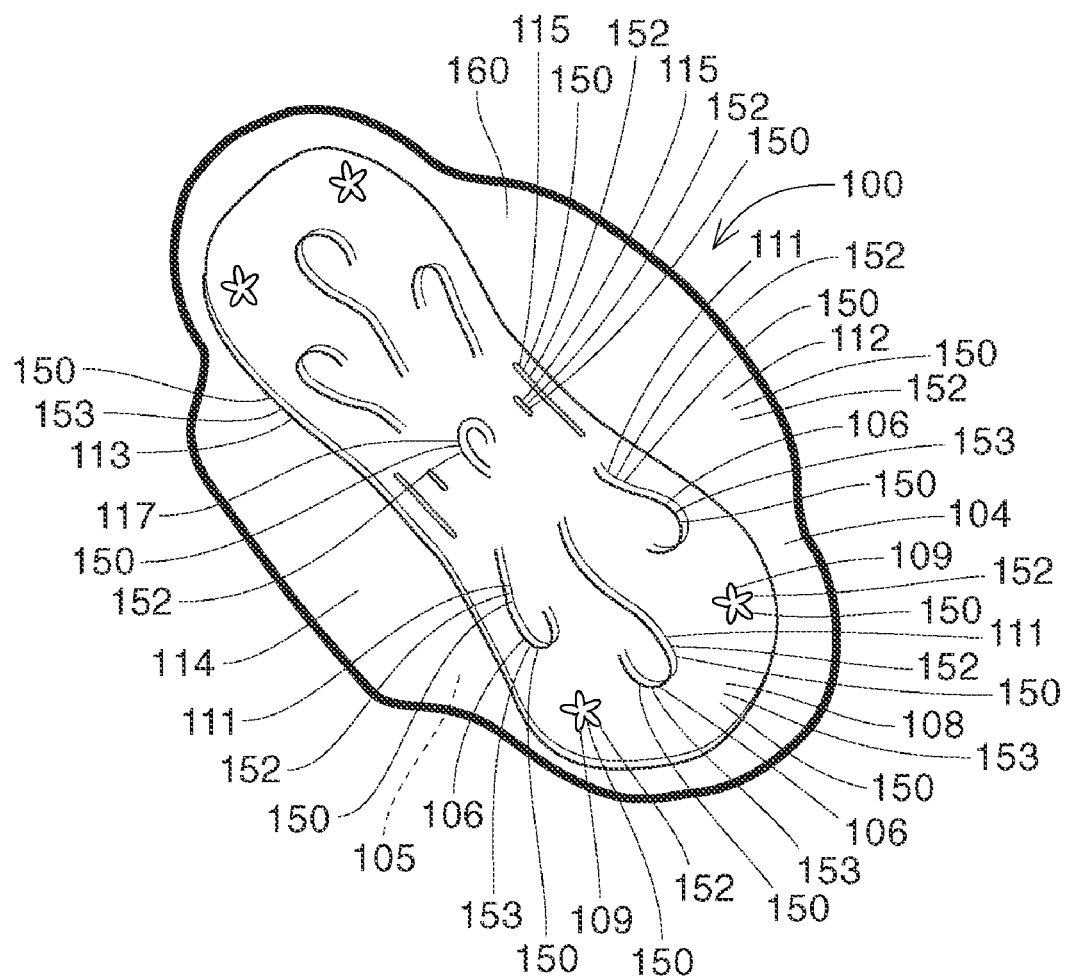
FIG. 4 is a top plan view of a miniature model.

The absorbent product 1 can include a miniature model 100 for delivering the product information of the absorbent article 20 to consumers. FIG. 4 illustrates a top plan view of a miniature model 100. In certain embodiments, the miniature model refers to an article which is a small copy of the absorbent article contained in the package. The miniature model 100 can have a first surface 104 and a second surface 105 opposing the first surface 104. As shown in FIG. 4, the first surface 104 can include a mimic portion 150 adapted to depict at least a part of a three-dimensional feature 36 of the absorbent article 20. Additionally or alternatively, the mimic portion 150 may further depict at least a part of the two-dimensional feature 38 of the absorbent article 20.

In certain embodiments, the mimic portion 150 may include two-dimensional indicia 152 that can be visible from the first surface 104. The two-dimensional indicia 152 may comprise a color portion. The color portion can be any suitable color, such as, the color portion may include a vibrant color portion (e.g., blue, yellow, pink), a contrasting color portion, a shade color portion (e.g., gray, light green, light blue), a gradation color portion, a gloss color portion, a matte color portion, and the like. In addition, the first color portion 112 can be emphasized by a color such as, e.g., a vibrant color, a contrasting color over white background, and/or shading.

In certain embodiments, the first color portion of the two-dimensional indicia 152 can depict the three-dimensional feature 36 of the absorbent article 20. For example, the first color portion can depict a three-dimensional feature 36 that is an embossment, a perforation, a channel, a convex, an aperture, a peripheral boundary, and the like. As shown in FIGS. 2 and 4, a plurality of the first color portions 111 can depict the channels 28 of the sanitary napkin 20, such as, e.g., by providing a perception of the depth formed by the channels 28. In addition, as shown in FIGS. 2 and 4, a plurality of the first color portions 115 can mimic the channels 33 of the sanitary napkin 20. In certain embodiments, the first color portions 111 and 115 can be printed with a gradation color so as to appear three-dimensional when printed on a generally flat surface. Referring to FIG. 4, the first color portions 111 and 115 can be colored with a gradation color of gray. In certain embodiments, the first color portion 112 can depict the peripheral boundary 50 of the sanitary napkin 20. As shown in FIGS. 2 and 4, the first color portion 113 can depict the convex portion 29 of the sanitary napkin 20, such as, for example, by depicting the shading formed by the thickness difference between the convex portion 29 and the peripheral region 34 when sanitary napkin 20 is viewed in three dimensions. The first color portion can be provided on the first surface 104 of the miniature model 100 by any suitable printing methods or technologies, including, but not limited to, gravure printing, flexo printing, offset printing, ink jet printing, and the like.

In certain embodiments, the second color portion of the two-dimensional indicia 152 can depict the two-dimensional feature 38 of the absorbent article 20. Referring to FIG. 4, a plurality of the second color portions 109 can depict at least a part of the color signal 44 of the two-dimensional feature 38. In addition, the second color portion 117 can depict the color signal 47 of the two-dimensional feature 38. The second color portion can be provided on the first surface 104 by any suitable printing methods or technologies, including, but not limited to, gravure printing, flexo printing, offset printing, ink jet printing, and the like. In certain embodiments, the second color portion can be provided with a color that is identical with or at least similar to the color of the color signal 44 such that consumers can recognize the second color portion 109 depicts the color signal 44 of the absorbent article 20. As shown in FIGS. 2 and 4, the color of the second color portion 117 and that of the color signal 47 can be identical to each other.

In certain embodiments, the mimic portion 150 may comprise a three-dimensional configuration 153. In addition, the three-dimensional configuration 153 may be mechanically formed on the first surface 104 of the miniature model 100. The three-dimensional configuration 153 can be any suitable configuration, such as, e.g., an embossment portion, a perforation portion, a convex portion, a concave portion or a combination thereof.

In certain embodiments, the three-dimensional configuration 153 can depict the three-dimensional feature 36 of the absorbent article 20. As shown in FIGS. 2 and 4, a plurality of embossment portions 106 can depict the channels 28 of the sanitary napkin 20. For example, in certain embodiments, the convex portion 108 can depict the convex portion 29 of the sanitary napkin 20 by showing the thickness difference from its surrounding peripheral region 114. In addition, the convex portion 108 may be thicker than its surrounding peripheral region 114.

The three-dimensional configuration 153 of the mimic portion 150 may be formed in any suitable manner, such as, e.g., embossing, compressing, or carving the material 160. In certain embodiments, the formed material 160 can then be cut by means known in the art into the shape of a sanitary napkin contour showing its perspective view (see FIG. 4).

In certain embodiments, the mimic portion 150 can include one or more two-dimensional indicia 152 and one or more three-dimensional configurations 153. In addition, the three-dimensional configuration 153 may be substantially aligned with the two-dimensional indicia 152. "Substantially aligned" refers to an embodiment wherein the two-dimensional indicia 152 and the three-dimensional configuration 153 are located at the same position or at a very close position. As described above, as shown in FIG. 4, a plurality of the first color portions 111 can depict the channels 28. In certain embodiments, such as shown in FIG. 4, the embossment portion 106 is located very close to the first color portion 111 so that consumers can recognize both the embossment portion 106 and the first color portion 111 represent the channels 28 of the sanitary napkin 20. In general, the embossment 106 can have a maximum dimension of from about 1 mm to about 30 mm, measured in a maximum dimension. The embossment 106 can have a maximum depth of from 0.1 mm to about 5 mm which is smaller than the thickness of the miniature model.

The absorbent article 20 may be provided with at least one color and the miniature model 100 may be provided with at least one color corresponding to the color(s) of the absorbent article 20. The use of the same or similar color in the miniature model 100 to the color of the absorbent article 20 may be perceived as a signal for the consumers to identify the absorbent product in a retail outlet. It may make it easy for the consumers to correctly choose the right absorbent article.

The absorbent article 20 and the miniature model 100 each have a periphery. The shape of the periphery of the miniature model 100 may be substantially identical with the periphery of the absorbent article 20. That is, the periphery of the miniature model 100 is adapted to depict the periphery of the absorbent article 20.

The two-dimensional indicia 152 and the three-dimensional configuration 153 can be achieved in any order, or simultaneously. In one embodiment, the two dimensional indicia 152 may be formed first, and then the two dimensional indicia 152 (or its adjacent area) may be embossed to form a three-dimensional configuration 153. In another embodiment, the three-dimensional configuration 153 may be formed first, and then the three-dimensional configuration 153 (or its adjacent area) may be colored to form the two dimensional indicia 152. In consequence, the three-dimensional configuration 153 is registered with the two dimensional indicia 152.

The miniature model 100 may be made of any suitable materials. For example, the miniature model material 160 may be made of plastic, a carton, a metal, clay, rubber, a mixture thereof, or any other suitable material. In certain embodiments, the materials used for the topsheet 22, the absorbent core 24 or the backsheet 26 may be used for the miniature model 100, such that the miniature model 100 looks more similar to the absorbent article 20. The miniature model 100 can have more than one material. The miniature model 100 may be layer-distinguish model from a piece of release paper wrapper (RPW) or the topsheet on the package. The miniature model 100 may be partially trimmed to show the internal material such as the absorbent core 24.

Figure 5:
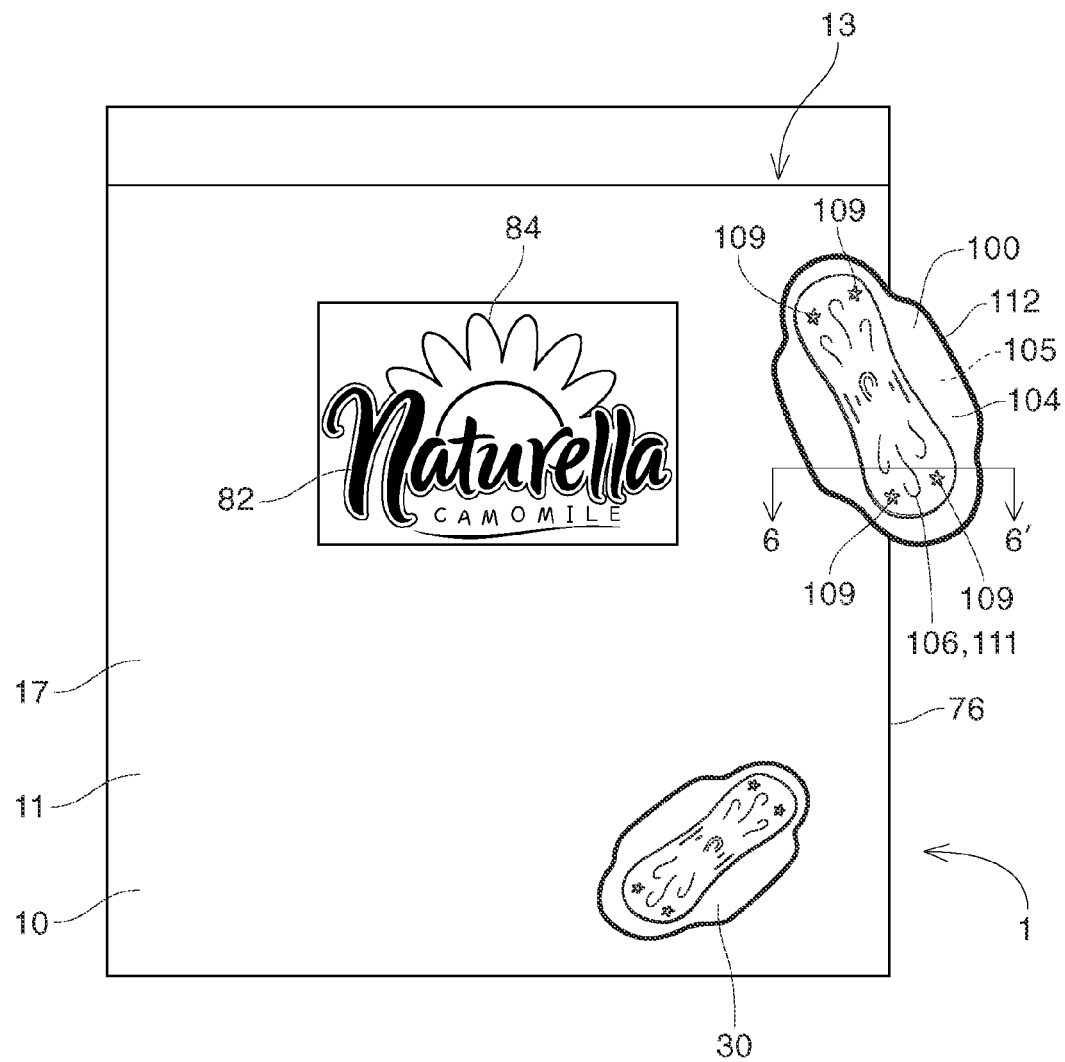
FIG. 5 is a front plan view of an absorbent product including a package and a miniature model.

FIG. 5 illustrates a front plan view of the absorbent product 1 comprising a package 10 which contains a plurality of sanitary napkins 20, and a miniature model 100 attached to the exterior surface 17 of the package 10. As shown in FIG. 5, the package 10 comprises general printed information on the exterior surface 17 such as the brand name 82 and a flower logo 84. In certain embodiments, the package 10 can further include a mimic image 30 of the sanitary napkin 20 on the exterior surface 17. The mimic image 30 can provide a perspective view of the absorbent article 20 contained in the package 10. In certain embodiments, the mimic image 30 can be a graphic or a picture of the absorbent article, for example, a sanitary napkin 20. In addition, or alternatively, the mimic image 30 can be printed with an appropriate color such as a vibrant color, a contrasting color, a shade, a gradation, a gloss, a matte, and the like so as to appear three-dimensional when printed on a generally flat surface of the package 10.

Figure 6:
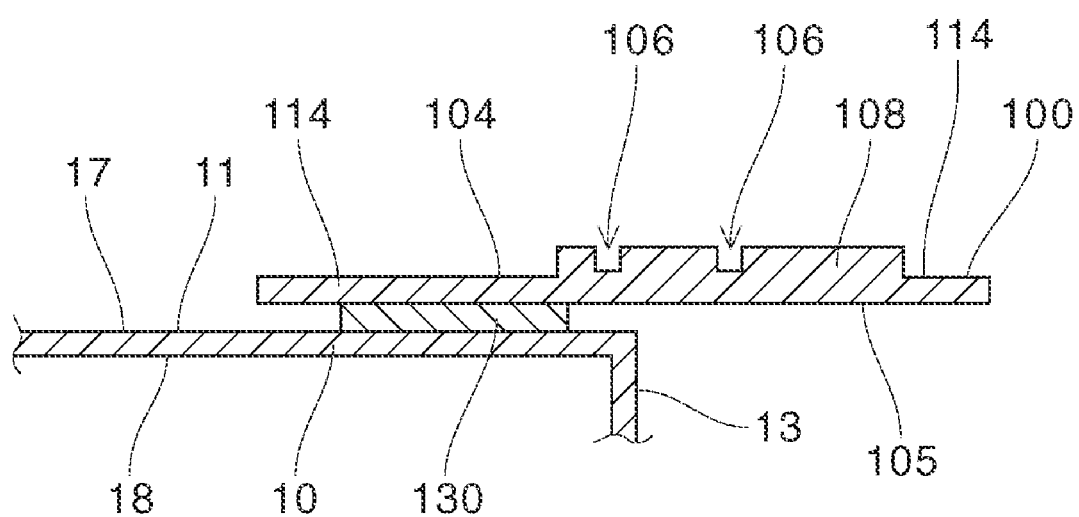
FIG. 6 is a cross-sectional view of the absorbent product of FIG. 5 along line 6-6'.

FIG. 6 illustrates a cross-sectional view of the miniature model 100 attached to the exterior surface 17 of the package 10 shown in FIG. 5 along line 6-6'. As shown in FIG. 5, in certain embodiments, the miniature model 100 may be attached to the exterior surface 17 such that a part of the miniature model 100 protrudes outside the edge 76 of the package 10. Alternatively, the miniature model 100 may be attached to the exterior surface 17 such that the whole miniature model 100 is within the edges of the package 10. In certain embodiments, the second surface 105 of the miniature model 100 is attached to the exterior surface 17 of the package 10 via an attachment device 130. The attachment device can include, for example, an adhesive, a double-sided adhesive tape, a mechanical fastener, and the like. Adhesives may be any suitable adhesive, such as, e.g., pressure sensitive adhesives, non-pressure sensitive adhesives, hot melt adhesives, and the like. Any adhesive materials known in the art can be used for the adhesive such as SIS (styrene-isoprene-styrene block copolymer), SBS (styrene-butadiene-styrene block copolymer), polyolefin, and the like. Mechanical fasteners can be any suitable mechanical fastener, such as, e.g., described in U.S. Pat. No. 4,959,265 by 3M which describes a pressure-sensitive adhesive tape fastener, the backing of which has an array of bluntly pointed stems protruding beyond the pressure-sensitive adhesive. In certain embodiments, the miniature model 100 may be detachably attached to the package 10 with a suitable detachable adhesive material. Such a detached miniature model 100 can be displayed in the shelf separated from the package 10. Furthermore, when consumers can take the detached miniature model 100 to the retail outlet, they can easily identify the desired product easily for purchase by comparing the detached miniature model 100 and the product at the retail outlet.

The miniature model 100 may not need to be attached to the package of the absorbent article 20. The miniature model 100 can be contained inside the package of the absorbent article. The miniature model 100 can be on a display at a retail outlet. The miniature model 100 can be mailed by the consumers to the manufacturer as a coupon. The miniature model 100 may be contained inside the package 10.

In certain embodiments, the second surface 105 of the miniature model 100 may be unprinted, or may comprise additional information such as, for example, text or an image, such as directions on how to use the absorbent article 20, advice for menstruating women, or an advertisement of consumer products.

The size of the miniature model 100 is designed so as to occupy from about 5% to about 50% of the area of the panel to which the miniature model 100 is attached (e.g., the front panel 11, the rear panel 12, the side panels 13 and 14, the top panel 15 or the bottom panel 16). In general, the miniature model 100 can range from about 1 cm to about 10 cm, measured in a maximum dimension of from one peripheral boundary to the other. The miniature model 100 can be disposed on any face of a package 10, but can be most useful when disposed on an externally visible face, i.e., a front surface 11 which is intended to be outwardly oriented with respect to a retail shelf.

The size of the miniature model 100 is about from about 2% to about 50%, or from about 5% to about 30% of that of the absorbent article 20. The size can be measured by the area of the absorbent article 20 and the miniature model 100.

In certain embodiments, the absorbent product 1 can include a miniature model 100 comprising a mimic portion 150. The mimic portion 150 can depict at least a part of a three-dimensional feature 36 of the absorbent article 20. The mimic portion 150 may further depict at least a part of the two-dimensional feature 38 of the absorbent article 20. As a result, the miniature model 100 can deliver product information of the absorbent article 20 in the package 10 to consumers. Furthermore, in certain embodiments, the miniature model 100 may appear as if it jutted out of the package 10 because the miniature model 100 is made of a material which is separate from the package 10. In consequence, the absorbent product 1 is useful for enhancing consumer acceptance compared to ordinary displays for absorbent articles.

It is understood that the examples and embodiments described herein are for illustrative purpose only and that various modifications or changes will be suggested to one skilled in the art without departing from the scope of the present invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent product comprising:
    (i) a package having an exterior surface and an interior surface, the interior surface defining an interior space,
    (ii) at least one absorbent article being contained within the interior space, the absorbent article having a body-facing surface, a garment-facing surface, the absorbent article having at least one dimensional feature viewable from the body-facing surface, and
    (iii) a miniature model having a first surface and a second surface opposing the first surface, the first surface having a mimic portion being adapted to depict at least a part of the dimensional feature of the absorbent article;
        wherein the dimensional feature depicted by the mimic portion is visible from the body facing side of the absorbent article and is selected from the group consisting of a colored part of the absorbent article, a plurality of color signals, an embossment, a perforation, a channel, an aperture, and combinations thereof.

2. The absorbent product of claim 1, wherein the second surface is attached to the exterior surface of the package.

3. The absorbent product of claim 1, wherein the mimic portion includes one or more two-dimensional indicia, the two-dimensional indicia being a color portion that is visible from the first surface of the miniature model.

4. The absorbent product of claim 1, the mimic portion further including a three-dimensional configuration substantially aligned with the two-dimensional indicia.

5. The absorbent product of claim 1, wherein the dimensional feature of the absorbent article is a three-dimensional feature selected from the group consisting of an embossment, a perforation, a channel, an aperture, and combinations thereof; and the mimic portion includes a three-dimensional configuration being adapted to depict the three-dimensional feature.

6. The absorbent product of claim 1, the package comprising a mimic image on the exterior surface thereof, the mimic image being adapted to depict the absorbent article contained in the package.

7. The absorbent product of claim 1, the miniature model being detachably attached to the package.

8. The absorbent product of claim 1, the absorbent article and the miniature model each having a periphery, wherein the periphery of the miniature model is adapted to depict the periphery of the absorbent article.

9. The absorbent product of claim 1, wherein the miniature model has a size of from about 2% to about 50% of a size of the absorbent article.

10. The absorbent product of claim 1, wherein a plurality of the dimensional features viewable from the body-facing surface form a flower petal pattern.

11. An absorbent product comprising:
(i) a package having an exterior surface and an interior surface, the interior surface defining an interior space;
(ii) at least one absorbent article being contained within the interior space, the absorbent article having a body-facing surface, a perimeter, a garment-facing surface, the absorbent article having at least one dimensional feature viewable from the body-facing surface and within the perimeter of the absorbent core; and
(iii) a miniature model having a first surface and a second surface opposing the first surface, the first surface having a mimic portion being adapted to depict at least a part of the dimensional feature of the absorbent article.

12. The absorbent product of claim 11, wherein the dimensional feature depicted by the mimic portion is visible from the body facing side of the absorbent article and is selected from the group consisting of a colored part of the absorbent article, a plurality of color signals, a three dimensional feature of the absorbent article, and combinations thereof.

13. The absorbent product of claim 12, the three-dimensional configuration being an embossment portion, a perforation portion, a convex portion, a concave portion or a combination thereof.

14. An absorbent product, comprising:
(i) a package having an exterior surface and an interior surface, the interior surface defining an interior space;
(ii) an absorbent articles contained within the interior space, the absorbent article comprising a tampon and being individually wrapped; and
(iii) a mimic portion associated with the package, the mimic portion depicting both a three-dimensional feature and a two-dimensional feature of the absorbent article, wherein the mimic portion itself comprises a three-dimensional configuration.

15. The absorbent article of claim 14, wherein the three-dimensional feature depicts a shape or the absorbent article and/or portion thereof.

16. The absorbent article of claim 14, wherein the two-dimensional feature comprises a color.

17. The absorbent article of claim 16, wherein the color is selected from the group consisting of blue, green, purple, and combinations thereof.

18. The absorbent article of claim 14, wherein the two-dimensional feature comprises a first color and a second color.

19. The absorbent article of claim 14, wherein the mimic portion three-dimensional configuration comprises at least one of an embossment portion, a convex portion, and a concave portion.

20. The absorbent article of claim 14, wherein the mimic portion is made from a material comprising a carton material.

21. An absorbent product, comprising:
(i) a package having an exterior surface and an interior surface, the interior surface defining an interior space;
(ii) an absorbent articles contained within the interior space, the absorbent article comprising a tampon and being individually wrapped; and
(iii) a mimic portion associated with the package, the mimic portion depicting one or more features of the absorbent article, wherein the mimic portion itself comprises a three-dimensional configuration, and wherein the mimic portion is made from a material comprising a carton material.

* * * * *